(12) United States Patent
Sung et al.

(10) Patent No.: US 10,888,804 B2
(45) Date of Patent: Jan. 12, 2021

(54) METHOD FOR SEPARATING AND WASHING OF MICROPARTICLES VIA A STRATIFIED COFLOW OF NON-NEWTONIAN AND NEWTONIAN FLUIDS

(71) Applicant: Korea Advanced Institute of Science and Technology, Daejeon (KR)

(72) Inventors: Hyung-Jin Sung, Daejeon (KR); Byung-Hang Ha, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 597 days.

(21) Appl. No.: 15/510,071

(22) PCT Filed: Jun. 30, 2016

(86) PCT No.: PCT/KR2016/006991
§ 371 (c)(1),
(2) Date: Mar. 9, 2017

(87) PCT Pub. No.: WO2017/126755
PCT Pub. Date: Jul. 27, 2017

(65) Prior Publication Data
US 2018/0028940 A1    Feb. 1, 2018

(30) Foreign Application Priority Data

Jan. 22, 2016    (KR) .......................... 10-2016-0008170

(51) Int. Cl.
*B01D 21/00*    (2006.01)
*B01L 3/00*    (2006.01)
(Continued)

(52) U.S. Cl.
CPC .............. *B01D 21/006* (2013.01); *B01L 3/00* (2013.01); *B01L 3/502753* (2013.01);
(Continued)

(58) Field of Classification Search
CPC ..... B01D 43/00; B01L 3/00; B01L 3/502753; B01L 3/502776; B01L 2400/0487;
(Continued)

(56) References Cited

U.S. PATENT DOCUMENTS 3,819,270 A * 6/1974 Hirschfeld ............... G01N 1/38
356/39
3,822,095 A * 7/1974 Hirschfeld ......... G01N 15/1434
356/39

(Continued)

FOREIGN PATENT DOCUMENTS

JP    2004-154747 A    6/2004
WO    2015/116990 A1    6/2015

OTHER PUBLICATIONS

Nam et al. Microfluidic device for sheathless particle focusing and separation using a viscoelastic fluid. Journal of Chromatography A, 1406 (2015) 244-250. (Year: 2015).*

(Continued)

*Primary Examiner* — Katherine Zalasky McDonald
(74) *Attorney, Agent, or Firm* — Medler Ferro Woodhouse Mills PLLC

(57) ABSTRACT

The present invention relates to a method for separating and washing microparticles via a stratified co-flow of non-Newtonian fluid and Newtonian fluid, wherein the Newtonian fluid as well as the non-Newtonian fluid may flow into a transfer channel formed in a fluid chip at a predetermined flow rate ratio matching with an effective diameter of the target particles contained in the non-Newtonian fluid, thereby inducing a change in positions of particle focusing points with respect to the target particles within the stratified co-flow thereof formed in the transfer channel. As a result, it is possible to more easily separate only the target particles among the microparticles contained in the non-Newtonian fluid toward the Newtonian fluid without using an additional (Continued)

device and human power, or transfer the target particles contained in the non-Newtonian fluid toward the Newtonian fluid for washing the same. Accordingly, since native biofluids used in the studies and clinical experiments are mostly non-Newtonian fluid, it is possible to directly separate and wash the target particles without a need of changing a solution for containing cells/particles or additional diluting the same for executing experiments. If the native biofluids as the non-Newtonian fluid lack a relaxation time, any artificial polymer could be simply added thereto in order to increase the relaxation time, thereby greatly increasing an amount of treatment per time. Further, since high working efficiency can be achieved in a wide range of flow rate, high efficient separation and washing processes may be achieved by a simple hand work of pushing and pumping an injector alone, without any accurate pumping device.

5 Claims, 4 Drawing Sheets

(51) Int. Cl.
  G01N 15/10 (2006.01)
  G01N 15/02 (2006.01)
  G01N 35/08 (2006.01)
  G01N 15/00 (2006.01)
  C07C 31/22 (2006.01)
  C08F 26/10 (2006.01)
  G01N 33/49 (2006.01)

(52) U.S. Cl.
  CPC .... B01L 3/502776 (2013.01); G01N 15/0255 (2013.01); G01N 15/1056 (2013.01); G01N 33/491 (2013.01); G01N 35/08 (2013.01); B01L 2400/0487 (2013.01); C07C 31/225 (2013.01); C08F 26/10 (2013.01); G01N 2015/0053 (2013.01); G01N 2015/0065 (2013.01); G01N 2015/1081 (2013.01); G01N 2015/1087 (2013.01)

(58) Field of Classification Search
  CPC ........... G01N 15/0255; G01N 15/1056; G01N 33/491; G01N 35/08; G01N 2015/0053; G01N 2015/0065; G01N 2015/1081; G01N 2015/1087; C08F 26/10; C07C 31/225
  See application file for complete search history.

(56) References Cited

U.S. PATENT DOCUMENTS

| | | | | |
|---|---|---|---|---|
| 6,432,630 B1* | 8/2002 | Blankenstein | ......... | B01D 57/02 435/4 |
| 8,361,415 B2* | 1/2013 | Di Carlo | ............ | B01D 21/0087 422/503 |
| 9,522,344 B2* | 12/2016 | Di Carlo | ........... | B01L 3/502761 |
| 2003/0159999 A1* | 8/2003 | Oakey | .................... | B01D 57/02 210/695 |
| 2008/0124779 A1* | 5/2008 | Oh | .................... | B01L 3/502761 435/173.9 |
| 2008/0194012 A1* | 8/2008 | Lee | .................. | B01L 3/502707 435/287.1 |
| 2008/0287911 A1* | 11/2008 | El-Nounou | ........ | A61M 25/0082 604/508 |
| 2009/0014360 A1* | 1/2009 | Toner | .................. | B01D 21/0087 209/208 |
| 2009/0078614 A1* | 3/2009 | Varghese | ............... | B03C 1/0332 209/39 |
| 2010/0178666 A1* | 7/2010 | Leshansky | .......... | G01N 15/1404 435/29 |
| 2011/0096327 A1* | 4/2011 | Papautsky | .......... | B01D 21/0087 356/335 |
| 2013/0228530 A1* | 9/2013 | Di Carlo | ........... | B01L 3/502761 210/767 |
| 2014/0065688 A1 | 3/2014 | Murthy et al. | | |
| 2014/0374324 A1* | 12/2014 | Papautsky | ......... | B01L 3/502753 209/132 |
| 2015/0268244 A1* | 9/2015 | Cho | .................... | G01N 15/1429 435/7.23 |
| 2016/0123858 A1* | 5/2016 | Kapur | .................. | G01N 1/4077 435/30 |
| 2016/0339434 A1* | 11/2016 | Toner | ................. | B01L 3/502776 |
| 2017/0052107 A1* | 2/2017 | Di Carlo | ................ | B01D 12/00 |

OTHER PUBLICATIONS

Shin et al. Continuous separation of microparticles in a microfluidic channel via the elasto-inertial effect of non-Newtonian fluid. Lab Chip, 2012, 12, 1347-1354. (Year: 2012).*

Avishay et al. The rheologic properties of erythrocytes: a study using an automated rheoscope. Rheol Acta (2007) 46:621-627. (Year: 2007).*

Peskin, Brian. "Parent Essential Oils (PEOs): The Difference," available at <http://brianpeskin.com/pdf/reports/PEO-Info.pdf>, accessed Aug. 27, 2019, 24 pages. (Year: 2019).*

Kang et al. DNA-based highly tunable particle focuser. Nat. Commun. 4 (2013) 1-8, 2567. (Year: 2013).*

English translation of the International Search Report for PCT/KR2016/006991, dated Oct. 18, 2016.

Del Giudice et al., Lab on a Chip 15:1912-1922 (2015), published Feb. 20, 2015.

Gossett et al., Small 8(17):2757-2764 (2012), published Jul. 3, 2012.

Ha et al., Analytical Chemistry 88(8):4205-4210, published Mar. 28, 2016.

Lu et al., Analytical Chemistry 87:11523-11530 (2015), published Oct. 27, 2015.

Nam et al., Biomicrofluidics 9: 064117 (2015), published Dec. 23, 2015.

Yang et al., Lab on a Chip 11:266-273 (2011), published Oct. 25, 2010.

\* cited by examiner

METHOD FOR SEPARATING AND WASHING OF MICROPARTICLES VIA A STRATIFIED COFLOW OF NON-NEWTONIAN AND NEWTONIAN FLUIDS

CROSS-REFERENCE TO RELATED APPLICATIONS

This application is a national phase entry under 35 U.S.C. § 371 of PCT/KR2016/006991 filed on Jun. 30, 2016, which claims the benefit of the priority date of Korean Patent Application No. 10-2016-0008170 filed on Jan. 22, 2016, which is hereby incorporated by reference in its entirety for all purposes.

FIELD OF THE INVENTION

The present invention relates a method for separating and washing microparticles using a stratified co-flow of non-Newtonian fluid and Newtonian fluid, and more particularly, to a method for separating and washing microparticles via a stratified co-flow of non-Newtonian fluid and Newtonian fluid, which includes: separating target particles among the microparticles contained in non-Newtonian fluid toward Newtonian fluid, or transferring microparticles contained in non-Newtonian fluid toward Newtonian fluid for washing the same, by using a stratified co-flow of non-Newtonian fluid and Newtonian fluid.

BACKGROUND OF THE INVENTION

Separation and washing of microparticles, that is, particles or cells having a size of micrometer or less are important processes of experiment, which are widely used in biological studies and clinical trials. In order to efficiently analyze and diagnose microparticles, samples are subjected to separation, washing and labeling processes by moving the same to different test materials from each other.

As a representative example thereof, there is fluorescent staining of cells which is a protocol most widely used in the biological studies (references 1 and 2). The cells are placed in a test material containing a florescent dye dissolved therein and sufficiently combined with the florescent dye, then, moved to a fresh medium solution for subsequent studies. In this case, the cells are washed out by the fresh medium solution to remove a residue of the florescent dye. Such a washing process is necessary for optimizing results of dyeing. The reason is that, the florescent dye residue is harmful to the cells or may cause an undesired reaction with cell organelles (reference 3).

As another example thereof, there is a pre-treatment in immunological study that separates only leukocytes in whole blood (reference 4). Peripheral blood mononuclear cells (PBMCs), which are the most important subject for studying in immunology, are successfully separated by mixing the blood with a high density sucrose solution, then executing density gradient centrifugation.

Following this, a lysis buffer for pulverizing erythrocytes is mixed with the prepared solution to break the erythrocytes, and if necessary, neutrophils and eosinophiles may be further separated.

After completing the separation through centrifugation, the sucrose solution and lysis buffer should be removed from the sample. The reason is that, if the cells are exposed to these solutions for a long time, it would be fatal to the cells. Further, in order to improve investigation accuracy by increasing a purity of a leukocyte sample, debris derived from lysis and other cell-derived materials should be removed.

Washing of blood corpuscles is widely used in clinical applications. A representative example thereof may include a case of filtering polluted material such as lipid microemboli while recycling the blood into the body of a patient by auto-transfusion performed during a heart operation (reference 5). Occasionally, due to medicines, coagulation, activated leukocytes and platelets, blood plasma should be removed (references 6 and 7). Separation and washing of fine particles, that is, microparticles as well as cells may also become a necessary process in experiments using the above material, in order to prepare and extract samples (reference 8).

A conventional method for separating and washing the fine particles, that is, microparticles or cells is centrifugation.

However, since the cells are exposed to a great shear stress during centrifugation, they may be easily injured (reference 9). Furthermore, since the sample should be taken using a pipette, taking a high efficiency and high purity sample is substantially impossible.

Further, since the centrifugation is neither a whole automatic process nor conducted in a continuous mode, the above method has disadvantages in that a skilled person is required in order to take a high efficiency sample, and a treatment amount per one time is limited. When repeating the centrifugation several times, the above disadvantages may be reduced, however, another problem of requiring a longer time and greater costs may occur.

In order to overcome the above-described disadvantages, a variety of microfluidic techniques have been developed (references 10 and 11).

The microfluidic techniques may be classified into an active method and a passive method. The passive method uses only a hydraulic power inherent in microfluid flows. Accordingly, behavior of particles and flows is previously determined based on a shape of micro-channel, properties of particles and fluids, flow condition, or the like.

The passive method may include, for example, Pinched Flow Fractionation (references 12 and 13), Inertia and/or Dean Flow Fractionation (references 14 to 16), Micro Vortex Manipulation (reference 17), Deterministic Lateral Displacement (reference 18), Zweifach-Fung effect (reference 19), Filtration (references 20 to 23), Micro Hydrocyclone (reference 24), etc., which have been reported in the academic world.

On the other hand, the active method refers is a method for controlling particles by additionally utilizing an external force to allow the particles to pass across a flow line. For example, methods of using sound (references 25 and 26), magnetic force (references 27 and 28), light (references 29 and 30), dielectrophoretic force (references 31 to 33), etc. have been reported in the academic world.

All of these methods have advantages and disadvantages, respectively. In general, the passive method is easy to embody and operate, but involve low applicability and efficiency. On the other hand, the active method has excellent applicability and efficiency, but entails disadvantages of complicate and difficult in practical embodiments (reference 10).

Most of the microfluidic techniques for treating fine particles (microparticles/cells) currently developed in the art involve a limitation in that the sample should be diluted to achieve a high efficiency. This problem may be mitigated when treating a high flow rate, however, this method entails a disadvantage of spending a great amount of medium solution.

For example, an inertial microfluidic method (reference 34) has an innovative and remarkable abilities to treat a high flow rate and is able to separate/wash microparticles. However, the above method is effective for only a sample having a low particle density. Consequently, in order to properly apply to practical studies or clinical environments, abilities of treating a liquid sample having a high particle density are necessarily required.

DETAILED DESCRIPTION

Figure 1:
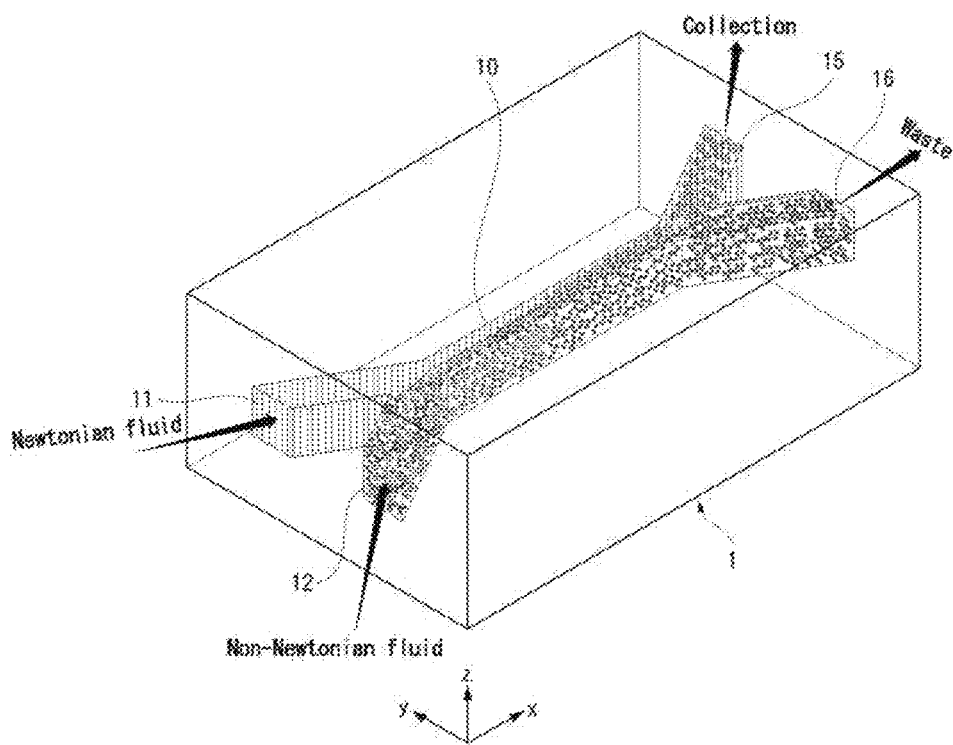
FIG. 1 is a three-dimensional perspective view schematically illustrating a fluid chip having a transfer channel formed therein for separating and washing microparticles via a stratified co-flow of non-Newtonian fluid and Newtonian fluid according to one embodiment of the present invention.

In order to solve the above-described problems, it is an object of the present invention to provide a method for separating and washing microparticles via a stratified co-flow of non-Newtonian fluid and Newtonian fluid, which includes: transferring only desired microparticles from native biofluids toward clean Newtonian fluid, by utilizing the stratified co-flow of non-Newtonian fluid and Newtonian fluid without using any centrifuge, and in particular, which enables to separate and wash microparticles with high efficiency by pumping a manual injector alone.

Technical Solution

In order to accomplish the above objects, there is provided a method for separating and washing microparticles via a stratified co-flow of non-Newtonian fluid and Newtonian fluid, including: flowing the non-Newtonian fluid and the Newtonian fluid in a stratified co-flow form within a transfer channel to induce a change in positions of particle focusing points at which forces acting on inside the transfer channel are balancing to each other; and separating or transferring target particles from microparticles included in the non-Newtonian fluid toward the Newtonian fluid.

Herein, preferably, the non-Newtonian fluid contains a polymer having sufficiently long relaxation time so as to have a larger elastic lift force with respect to the target particles than an inertial lift force, and the polymer is contained in a high concentration enough to have a transfer velocity of the target particles sufficient to pass across a flow line.

In addition, the non-Newtonian fluid may include at least one selected from natural biofluids consisting of blood, BC-lysed blood, serum or lymph.

Further, the non-Newtonian fluid may be formed by adding an artificial polymer so as to artificially have viscous elasticity.

Herein, preferably, the artificial polymer is a water-soluble polymer having a relaxation time of 1 millisecond (ms) or more, and the artificial polymer may include at least one selected from λ-DNA, polyethylene oxide (PEO) and polyvinyl pyrrolidone (PVP).

In addition, the Newtonian fluid may include a fluid having a larger inertial lift force with respect to the target particles than an elastic lift force.

Herein, wherein the Newtonian fluid may include any water-soluble solution for containing the target particles. For example, water, aqueous glycerin solution or phosphate buffer saline (PBS) may be used.

In addition, preferably, an area ratio of cross-sectional areas occupied by the non-Newtonian fluid and the Newtonian fluid in the transfer channel is about 1:1. The area ratio of cross-sectional areas occupied by the respective fluids is generally determined by a flow rate ratio and a viscosity ratio.

Further, preferably, the transfer channel is formed so as to have a size in proportion to a size of the effective diameter of the target particle.

Further, the transfer channel may have 1 or more of an aspect ratio (height/width) to the cross-sectional area thereof.

Further, preferably, the transfer channel is formed so as to have a length in inverse proportion to a flow velocity or elasticity number of the non-Newtonian fluid.

Further, preferably, the transfer channel has a length formed within a range of 1 L to 10 L, and the transfer channel has a minimum length L satisfying the following equation:

$$L = \frac{\pi \mu w^2}{\rho U_{max} d^2 f_L}$$

wherein, $U_{max}$ is a maximum channel velocity, is an experience proportional constant, w is a width of the transfer channel, d is an effective diameter of the target particle, μ is a viscosity of the fluid, and ρ is a density of the fluid.

Further, preferably, a minimum flow rate Q required for achieving inertial focusing within the minimum length L of the transfer channel satisfies the following equation:

$$Q \approx \frac{2\pi \mu h w^2}{3\rho L d^2 f_L}$$

wherein, h is a height of the transfer channel, w is a width of the transfer channel, and $f_L$ is an experience proportional constant.

Further, the transfer channel may be formed in a fluid chip in a straight line form, and the fluid chip may have a first inlet through which the Newtonian fluid inflows and a second inlet through which the non-Newtonian fluid inflows, which are formed in a front end portion of the channel at an interval with being decreased toward an inside at a predetermined angle therebetween so as to be joined with each other; and a first outlet through which the Newtonian fluid containing the target particles outflows and a second outlet through which the non-Newtonian fluid outflows, which are formed in a rear end portion of the channel at an interval with being increased toward an outside at a predetermined angle therebetween so as to be branched from each other.

Herein, the fluid chip may be made of any one selected from silicone-based polymers, plastics, glass, Si and metal.

In addition, the silicone-based polymers may include polydimethylsiloxane (PDMS).

Further, the plastics may include at least one selected from polymethyl methacrylate (PMMA), polypropylene (PP), cyclic olefin copolymer (COC) or polyethylene terephthalate (PETE) and polyvinyl chloride resin, polyethylene resin, polystyrene resin, polypropylene resin and acryl resin.

Furthermore, flow resistances at the first outlet and the second outlet may be adjusted by an alternation of design in a cross section of a flow path or utilizing a valve, so as to control a position of the flow line at which the non-Newtonian fluid and the Newtonian fluid are divided.

Advantageous Effects

According to the method for separating and washing microparticles via a stratified co-flow of non-Newtonian fluid and Newtonian fluid of the present invention, the Newtonian fluid as well as the non-Newtonian fluid may flow into a transfer channel formed in a fluid chip at a predetermined flow rate ratio matching with an effective diameter of the target particles contained in the non-Newtonian fluid, thereby inducing a change in positions of particle focusing points with respect to the target particles within the stratified co-flow thereof formed in the transfer channel. As a result, it is possible to more easily separate only the target particles among the microparticles contained in the non-Newtonian fluid toward the Newtonian fluid without using an additional device and human power, or transfer the target particles contained in the non-Newtonian fluid toward the Newtonian fluid for washing the same.

In addition, according to the method for separating and washing microparticles via a stratified co-flow of non-Newtonian fluid and Newtonian fluid of the present invention, since the native biofluids used in the studies and clinical experiments are mostly non-Newtonian fluid, it is possible to directly separate and wash the target particles without a need of changing a solution for containing cells/particles or additional diluting the same for executing experiments. If the native biofluids as the non-Newtonian fluid lack a relaxation time, any artificial polymer could be simply added thereto in order to increase the relaxation time, thereby greatly increasing an amount of treatment per time. Further, since high working efficiency can be achieved in a wide range of flow rate, high efficient separation and washing processes may be achieved by a simple hand work of pushing and pumping an injector alone, without any accurate pumping device.

Further, according to the method for separating and washing microparticles via a stratified co-flow of non-Newtonian fluid and Newtonian fluid of the present invention, the fluid chip having the transfer channel formed therein may be manufactured in a disposable form using cheap plastics or polymer materials. Therefore, production costs may be reduced and the inventive method can be applied to a variety of applications for general purposes at a low cost.

Hereinafter, preferred embodiments of the present invention will be described in detail with reference to the accompanying drawings, so as to assist those having ordinary skill in the art in a comprehensive understanding of the invention, and the present invention is not limited to the embodiments disclosed below. In the embodiments of the present invention, publicly known functions and configurations that are judged to be able to make the purport of the present invention unnecessarily obscure will not be described. Referring to the drawings, wherein like reference characters designate like or corresponding parts throughout the several views.

FIG. 1 is a three-dimensional perspective view schematically illustrating a fluid chip having a transfer channel formed therein for separating and washing microparticles via a stratified co-flow of non-Newtonian fluid and Newtonian fluid according to one embodiment of the present invention.

Referring to FIG. 1, a method for separating and washing microparticles via a stratified co-flow of non-Newtonian fluid and Newtonian fluid according to the present invention may include flowing the non-Newtonian fluid and the Newtonian fluid in a form of co-flow into a transfer channel 10 to induce a change in positions of particle focusing points at which forces acting on inside the transfer channel are balancing to each other, and separating or transferring target particles among the microparticles contained in the non-Newtonian fluid toward the Newtonian fluid.

Herein, the non-Newtonian fluid refers to a fluid containing a polymer which has a sufficiently long relaxation time so as to have a larger elastic lift force with respect to the target particles than an inertial lift force, and is contained in a high concentration enough to have a transfer velocity of the target particles sufficient to pass across a flow line.

Accordingly, the non-Newtonian fluid may include natural biofluids consisting of blood, BC-lysed blood, serum or lymph, as well as, may be formed by adding an artificial polymer to a sample fluid so as to artificially have viscous elasticity, that is, non-Newtonian properties.

In this regard, it is preferable that the artificial polymer includes any type of water-soluble polymers having a relaxation time of 1 millisecond (ms) or more, and for example, may include at least one selected from λ-DNA, polyethylene oxide (PEO) and polyvinyl pyrrolidone (PVP).

Meanwhile, the Newtonian fluid refers to a fluid having a larger inertial lift force with respect to the target particles than an elastic lift force, and may include any water-soluble solution for containing the target particles. For example, water, aqueous glycerin solution or phosphate buffer saline (PBS), etc. may be used.

However, the non-Newtonian fluid and Newtonian fluid are not particularly limited to the above-described materials. Of course, as described above, a variety of other fluids may be employed as the non-Newtonian fluid and Newtonian fluid so long as they can flow in a stratified co-flow form into the transfer channel 10 to induce a change in the positions of the particle focusing points, at which forces acting on inside the transfer channel 10 are balancing to each other, and separate or transfer the target particles contained in the non-Newtonian fluid toward the Newtonian fluid.

Meanwhile, the present embodiment illustrates a configuration in which the transfer channel 10 used for separating and washing microparticles by using a stratified co-flow of non-Newtonian fluid and Newtonian fluid is formed in a fluid chip 1 in a longitudinal direction thereof, wherein the transfer channel 10 includes: a first inlet 11 through which the Newtonian fluid inflows, and a second inlet 12 through which the non-Newtonian fluid inflows, which are formed in a front end portion of the channel at an interval with being decreased toward an inside at a predetermined angle of (Θ) therebetween so as to be joined with each other; and a first outlet through which the Newtonian fluid containing the target particles outflows and a second outlet through which the non-Newtonian fluid outflows, which are formed in a rear end portion of the channel at an interval with being increased toward an outside at a predetermined angle therebetween so as to be branched from each other.

Herein, the present embodiment illustrates that the fluid chip includes polydimethylsiloxane which is a silicone-based polymer.

However, the present invention is not particularly limited thereto, and of course, the fluid chip may include at least one selected from plastics, glass, Si or metals other than the silicone-based polymers.

Herein, the plastics may include at least one selected from polymethyl methacrylate (PMMA), polypropylene (PP), cyclic olefin copolymer (COC) or polyethylene terephthalate (PETE) and polyvinyl chloride resin, polyethylene resin, polystyrene resin, polypropylene resin and acryl resin.

Further, the present embodiment illustrates a configuration in which the transfer channel 10 has a width of 30 μm, a height of 54 μm and a length of 20 mm and includes the first inlet 11, the second inlet 12, a first outlet 15 and a second outlet 16, which are joined with and branched from each other in opposite end portions of the transfer channel at a predetermined angle (Θ) of about 60° therebetween, respectively.

As such, the present embodiment illustrates the configuration in which the transfer channel 10 is formed in a micro-scale so as to suitably separate and transfer fine particles including micro-scaled particles or cells contained in the non-Newtonian fluid, but it is not particularly limited thereto. Of course, such a transfer channel is manufactured and used in different scales to which the separation and transfer mechanism of the microparticles may be applied, which will be described below.

Further, as described below, a size of the transfer channel 10 may be diversely altered and applied depending on not only an effective diameter of the target particles included in the non-Newtonian fluid but also an elasticity number (EI EI) and a flow rate Q. Of course, each of the angles (Θ) between the first inlet 11 and the second inlet 12 and between the first outlet 15 and the second outlet 16 may be more diversely modified and applied, respectively.

Accordingly, the Newtonian fluid as well as the non-Newtonian fluid may flow into a transfer channel 10 formed in a fluid chip at a predetermined flow rate ratio matching with an effective diameter of the target particles contained in the non-Newtonian fluid, thereby inducing a change in positions of particle focusing points with respect to the target particles within the stratified co-flow thereof formed in the transfer channel. As a result, it is possible to more easily separate only the target particles among the microparticles contained in the non-Newtonian fluid toward the Newtonian fluid without using an additional device and human power, or transfer the target particles contained in the non-Newtonian fluid toward the Newtonian fluid for washing the same.

Hereinafter, with regard to the method for separating and washing microparticles via a stratified co-flow of non-Newtonian fluid and Newtonian fluid, theoretical backgrounds will be described with reference to FIGS. 2 and 3.

Figure 2:
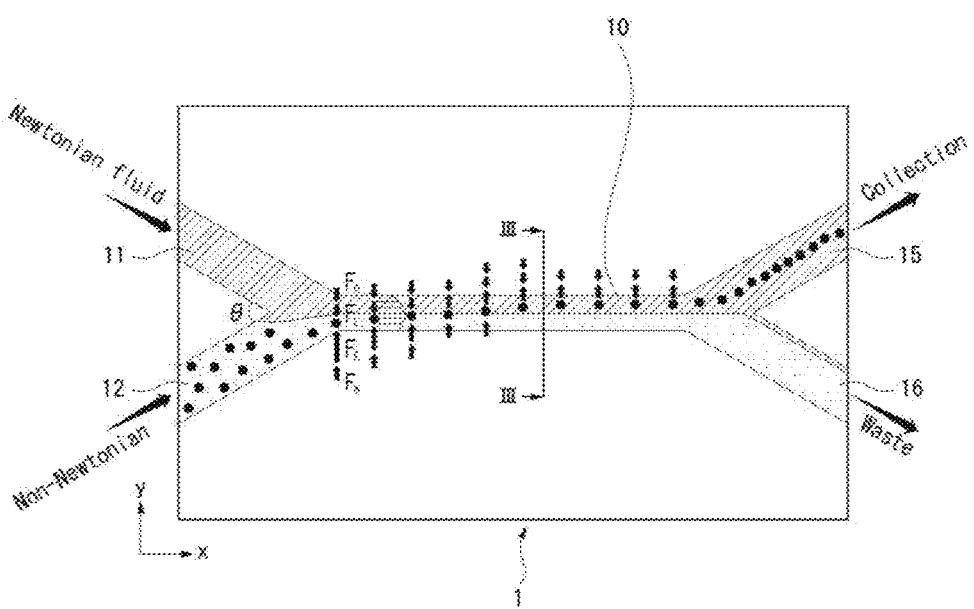
FIG. 2 is a plan view illustrating the fluid chip of FIG. 1.
Figure 3:
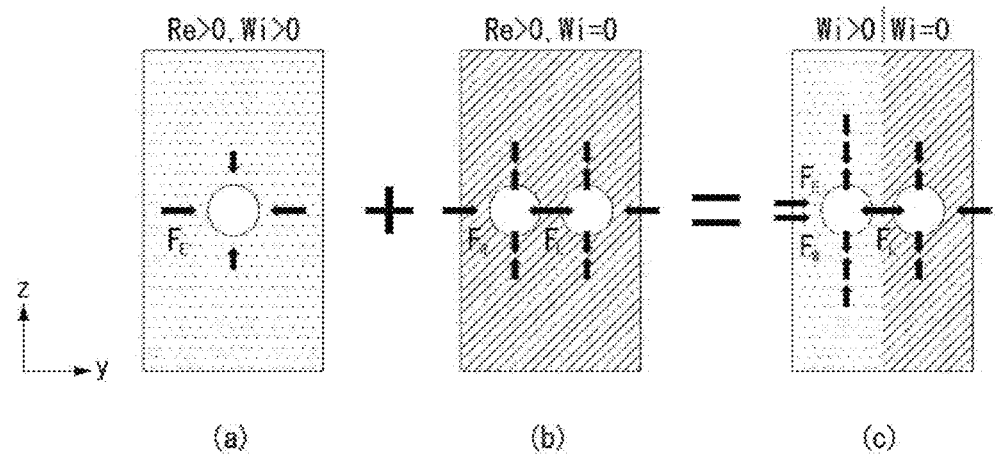
FIG. 3 is a cross-sectional schematic view of the transfer channel taken on line II-II of FIG. 2 for describing balancing points between forces passively focusing microparticles during flowing of non-Newtonian fluid and/or Newtonian fluid therein.

FIG. 2 is a plan view of the fluid chip shown in FIG. 1, and FIG. 3 is a cross-sectional schematic view of the transfer channel taken on line II-II of FIG. 2 for describing balancing points between forces passively focusing microparticles during flowing of non-Newtonian fluid and/or Newtonian fluid therein.

Referring to FIGS. 2 and 3, the balance between forces acting on the target particles contained in an elastic fluid within the transfer channel is as follows.

In the following description, Re is a Reynolds number of a channel flow, and Wi is a Weissenberg number of the channel flow.

As shown in FIG. 3(a), when the transfer channel is filled with only the non-Newtonian fluid containing the microparticles (Re>0.Wi>0), only elastic lift forces ($F_E$) may predominantly influence upon the microparticles, and therefore, transfer the microparticles toward a middle of the transfer channel (a center thereof in a width direction) (reference 35).

As shown in FIG. 3(b), when the transfer channel is filled with only the Newtonian fluid containing the microparticles (Re>0.Wi≈0), an inertial lift force ($F_L$) and a wall lift force ($F_W$) may predominantly influence upon the microparticles, and therefore, transfer the microparticles toward two balancing points formed at both sides adjacent to the middle of a channel wall having a wide area (reference 34).

Further, as shown in FIG. 3(c), when the non-Newtonian fluid and the Newtonian fluid which contain the microparticles together are flowing into the transfer channel while forming a stratified co-flow, all of the microparticles may transfer toward a single balancing point formed in the Newtonian fluid.

Gradual movement of the microparticles from the inlet of the transfer channel to the outlet thereof may be illustrated as shown in FIG. 2.

Herein, transfer of the microparticles may be determined by four types of forces, that is, the elastic lift force ($F_E$), the inertial lift force ($F_L$), the wall lift force ($F_W$) and a Stokes' drag force ($F_D$).

The Stokes' drag force ($F_D$) may be represented by Equation 1 below.

$$F_D = 3\pi\eta_s dV_P \qquad [\text{Equation 1}]$$

(wherein $\eta_s$ is a viscosity of the fluid, d is an effective diameter of the microparticle, and $V_p$ is a transfer velocity of the microparticle in a lateral direction.)

Therefore, the microparticles just inflow into the front end of the transfer channel through the first and second inlets may receive a force so as to be away from the wall. The reason is that, a sum of the elastic lift force ($F_E$) and the wall lift force ($F_W$) is larger than a sum of the inertial lift force ($F_L$) and the Stokes' drag force ($F_D$).

When the microparticles reached a boundary between two fluids, that is, the non-Newtonian fluid and the Newtonian fluid, the elastic lift force ($F_E$) and the inertial lift force ($F_L$) are combined to further push the target particles into the Newtonian fluid.

Finally, the microparticles are guided toward a balancing point between the inertial lift force ($F_L$) and the wall lift force ($F_W$), and then are focused within the Newtonian fluid.

That is, assuming that the elastic lift force ($F_E$) and the Stokes' drag force ($F_D$) would predominantly control the movement of particles in a direction across the flow line, the transfer velocity of the particles ($V_P$) regularly defined by an average flow velocity ($\overline{U_f}$) may be represented by Equation 2 below.

$$\frac{V_p}{\overline{U_f}} = \beta_P \frac{c}{c^*} Wi\left(\frac{d}{w}\right)^2 \quad \text{[Equation 2]}$$

(wherein $\beta_p$ is an experience proportional constant, w is a width of the transfer channel, and Wi is a Weissenberg number of non-Newtonian fluid. In addition, c is a polymer concentration, and $c^-$ is an overlapping concentration.)

Figure 4:
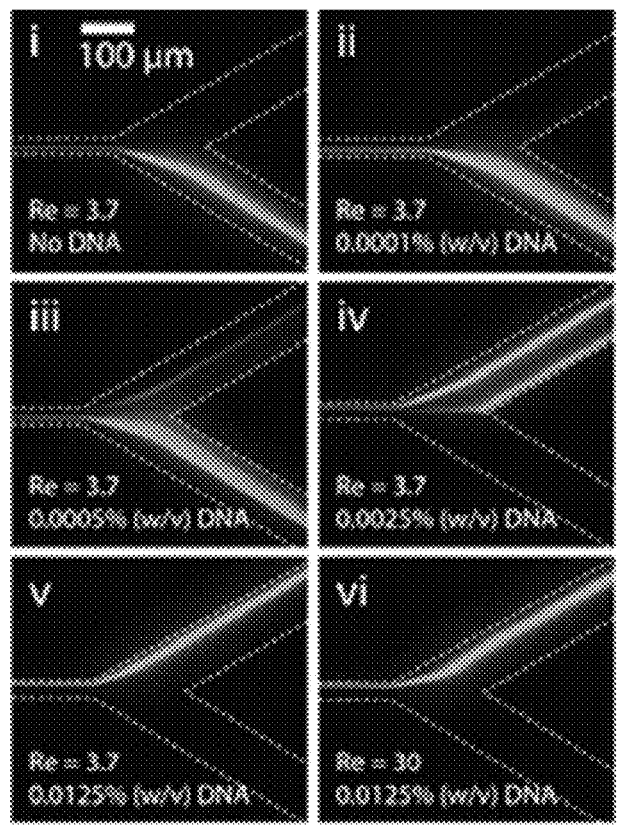
FIG. 4 is florescent microphotographs illustrating that a rate of transferring particles across a flow line is changed by a concentration of DNA contained in the non-Newtonian fluid.

Accordingly, in order to successfully separate and transfer the target particles from the non-Newtonian fluid to Newtonian fluid, a relaxation time of the polymer contained in the non-Newtonian fluid should be at least a predetermined level, that is, 1 milisecond (ms) or more, and the polymer should also have a sufficiently high concentration. Such a requirement may be demonstrated by experimental results in Experimental Example 1 below, which is shown in FIG. 4.

EXAMPLES

Example 1

In Experimental Example 1, an experiment was conducted to demonstrate that a rate of transferring particles across a flow line is changed by a concentration of DNA contained in the non-Newtonian fluid.

FIG. 4 are florescent microphotographs illustrating that the rate of transferring particles across the flow line is changed by the concentration of DNA contained in the non-Newtonian fluid.

Referring to FIG. 4, the non-Newtonian fluid (Aqueous k-DNA Solution) containing the microparticles and the Newtonian fluid (Aqueous Glycerin Solution) flow in a stratified co-flow form through the first inlet 11 and the second inlet 12 at a flow rate ratio of 1:1 into the transfer channel 10 (8.3 μL/min for i-v, 66.7 μL/min for vi).

In this case, it can be seen that a transfer rate of the microparticles is increased as λ-DNA concentration in the non-Newtonian fluid is increased, as shown in FIGS. 4(i) to 4(vi).

The above-described mechanism for separation or transfer of microparticles may be applicable to kinetic separation of particles according to a size thereof.

The transfer velocity of particles within the flow of the non-Newtonian fluid in a direction across the flow line is proportional to a square of the effective diameter of the microparticle (see Equation 2).

Therefore, the microparticles having a large effective diameter may transfer toward the middle part of the channel much more quickly while transferring the same distance along the flow line direction than the microparticles having a small effective diameter. Similarly, the microparticle having a large effective diameter may transfer toward the single balance focusing point within the flow of the Newtonian fluid much more quickly than the microparticles having a small effective diameter. The reason is that, the transfer velocity is proportional to a cube of the effective diameter of the microparticle (reference 36).

Meanwhile, design conditions of the transfer channel 10 and flow thereof may be as follows. In order to sufficiently create inertial/wall lift forces and therefore attain high efficiency separation or washing, the Reynolds number of a particle) ($R_v = Re(d/w)^2 = \rho U d^2/\mu w$) should be the first order or more.

In a case of the present embodiment, $R_p$ preferably belongs to a range of 1.2 to 12. In other words, as a size of the microparticle is decreased, the transfer channel should also be designed so as to have a smaller dimension while increasing a flow rate in plenty.

Meanwhile, when $R_p$ is 1 or less, effects due to the inertial lift force are insignificant. However, the separation or washing may be effectively executed by the inertial lift force due to in-depth diffusion of the non-Newtonian fluid.

In the present embodiment, the high efficient separation or washing is executed mostly when $R_p$ is 1 or more. However, of course, even the principle when $R_p$ is 1 or less, may also be included therein.

Meanwhile, since an aspect ratio (height/width) of the transfer channel is 1 or more, focusing points in the transfer channel should be compressed into two positions.

If the aspect ratio of the transfer channel is less than 1, the position and number of focusing points are changed, and would not be successful in achieving a compressive change of the focusing points intended by the present invention.

A flow rate ratio between the non-Newtonian fluid and the Newtonian fluid may be in such a range that an area occupied by non-Newtonian fluid flow is enough large to eliminate one of two focusing points. An area ratio occupied by these two fluid flows is mainly determined by the flow rate ratio and a viscosity ratio. If the non-Newtonian fluid and the Newtonian fluid have the substantially same average viscosity as each other, it is preferable that the flow rate ratio of the Newtonian fluid to the non-Newtonian fluid is within a range of 1:1 to 1:2 in an aspect of high efficiency separation.

In this regard, assuming that the non-Newtonian fluid and the Newtonian fluid have the substantially same average viscosity as each other, if the flow rate ratio of the Newtonian fluid to the non-Newtonian fluid is less than 1:1, an area occupied by the non-Newtonian fluid is large, such that a distance between the focusing position of the target particles and the position of other particles is decreased, resulting in a disadvantage such as a reduction in efficiencies. Meanwhile, if the flow rate ratio of the Newtonian fluid to the non-Newtonian fluid exceeds 1:2, the area occupied by the non-Newtonian fluid is small, such that a desired change in the particle focusing points is not sufficiently achieved, also resulting in a disadvantage such as a reduction in efficiencies.

Further, in order to ensure enough time that the target particles can reach a target focusing point, the transfer channel should be formed with at least a predetermined length.

However, in order to ensure no time that relatively small and undesired particles are gathered into the focusing point, the length of the transfer channel should not be too long.

Accordingly, it is preferable that the length of the transfer channel is determined within a range of 1 L to 10 L, and a minimum transfer channel length L may be calculated by Equation 3 below.

$$L = \frac{\pi \mu w^2}{\rho U_{max} d^2 f_L} \quad \text{[Equation 3]}$$

(wherein $U_{max}$ is a maximum flow velocity in the channel (up to 1.5 U of average flow velocity), $f_L$ is an experience proportional constant and known to have a value in a range of 0.02 to 0.05 when the aspect Ratio (height/width) alters from 0.5 to 2. In the case of the present invention, since a time period for particle transfer in the non-Newtonian fluid is also needed, a transfer channel having a longer length than the above range is required.)

Accordingly, if the length of the transfer channel is less than 1 L, the transfer of target particles for separating and washing the same may not smoothly proceed. If the length of the transfer channel exceeds 10 L, smaller particles than the target particles may be undesirably separated during the separation of target particles, hence causing a disadvantage of reducing a recovery rate and purity.

Meanwhile, a minimum flow rate for executing the inertial focusing within the transfer channel length L may be calculated by Equation 4 below.

$$Q \approx \frac{2\pi\mu hw^2}{3\rho L d^2 f_L} \quad \text{[Equation 4]}$$

For the flow of the non-Newtonian fluid, in order to transfer the target particles against the inertial lift force toward the flow of the Newtonian fluid, an elasticity number (EI) representing a relative intensity between the elastic lift force and the inertial lift force should be a predetermined value or higher. Herein, the elasticity number EI may be represented by Equation 5 below.

$$EI = \frac{Wi}{Re} = \frac{\lambda\mu(w+h)}{\rho w^2 h} \quad \text{[Equation 5]}$$

Equation 5 is effective when a viscosity is constant throughout the entire flow region. However, since the non-Newtonian fluid becomes a shear thinning or shear thickening state, the viscosity is not constant. Therefore, Equation 5 above may be proposed for reference only.

When the viscosity is set to 1.88 cP corresponding to that of an aqueous glycerin solution and used in the present embodiment, EI is calculated at approximately about 400.

Example 2

In Experimental Example 2, an experiment was conducted to separate polystyrene (PS) microparticles (spherical) having a diameter of 9.9 μm contained in the non-Newtonian fluid from particles having a diameter of 2.0 μm in the same fluid, then, move the separated particles into the Newtonian fluid.

In this regard, the fluid chip 1 made of PDMS-glass may be manufactured by existing soft lithography according to an SU-8 replica molding protocol.

In this regard, the PDMS fluid chip 1 may be manufactured by firstly mixing PDMS Base (Sylgard 184A, Dow Corning, Mich., USA) and a curing agent (Sylgard 184B, Dow Corning, Mich., USA) in a ratio of 10:1, pouring the mixture in an SU-8 mold, and curing the same in an oven at 95° C. for 2 hours or more.

In this case, the transfer channel 10 for flowing the fluid provided in the PDMS fluid chip 1 may be fabricated in the form of a closed channel as described above. Accordingly, a glass slide (not shown) to form a bottom surface of the transfer channel is prepared. The glass is combined with the transfer channel through oxygen plasma treatment.

Figure 5:
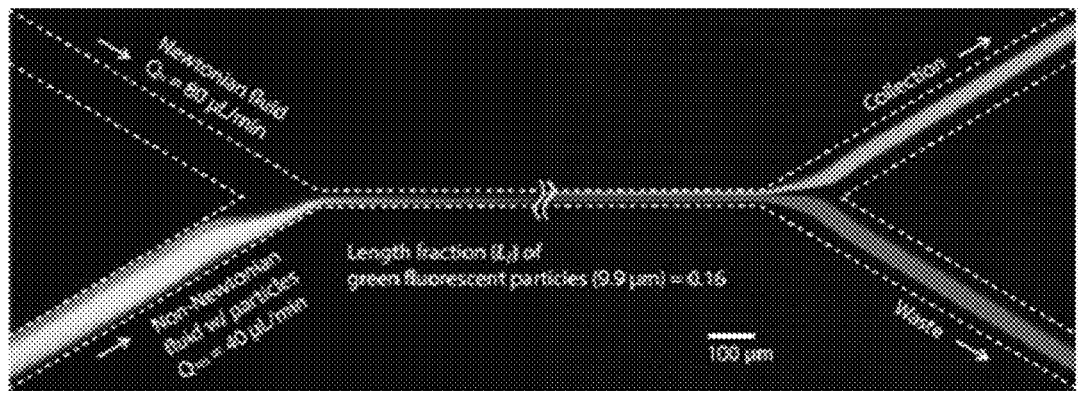
FIG. 5 is a combined florescent microphotograph illustrating a result of separating the particles in flow of a non-Newtonian fluid sample having a particle density corresponding to a length fraction (=0.16) of a microfluidic channel.
Figure 6:
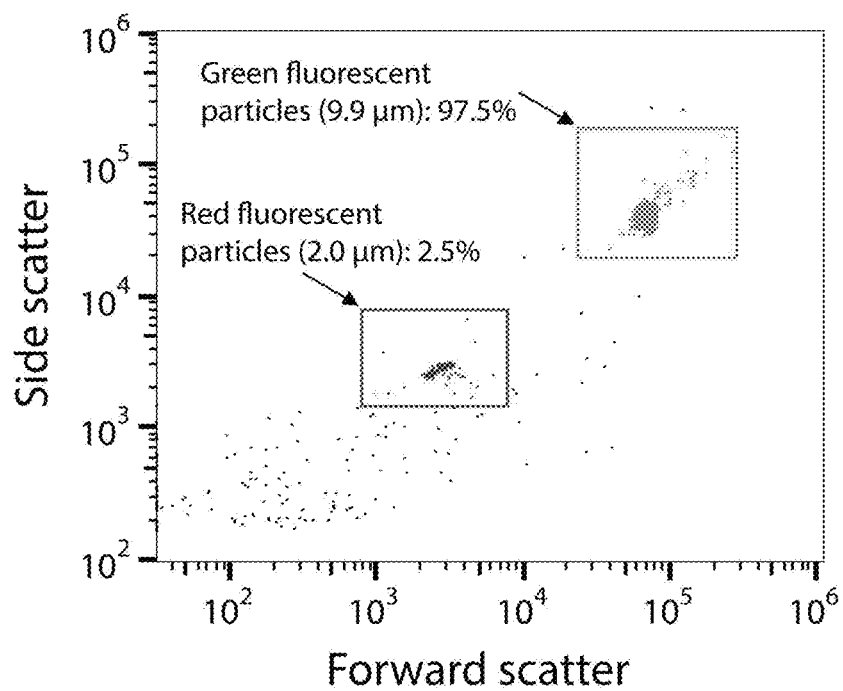
FIG. 6 is a graph illustrating results obtained by measuring a ratio of relative numbers between two particles in a sample captured at a first outlet by flow cytometry.
Figure 7:
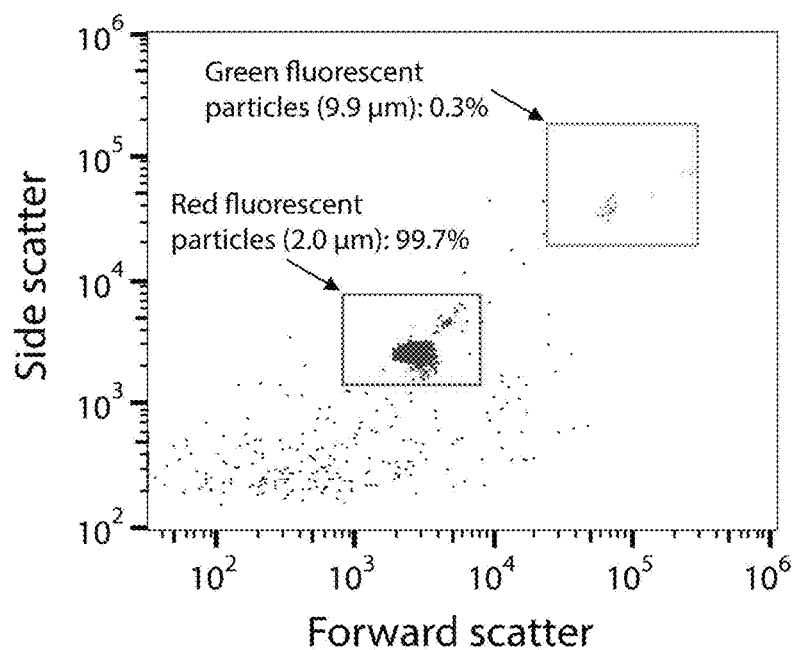
FIG. 7 is a graph illustrating results obtained by measuring a ratio of relative numbers between two particles in a sample captured at a second outlet by the flow cytometry.

FIG. 5 is a combined fluorescent microphotograph illustrating a result of separating the particles in flow of a non-Newtonian fluid sample having a particle density corresponding to the length fraction (=0.16) of the transfer channel 10, FIG. 6 is a graph illustrating results obtained by measuring a ratio of relative numbers between two particles in the sample captured at the first outlet 15 by flow cytometry, and FIG. 7 is a graph illustrating results obtained by measuring a ratio of relative numbers between two particles in the sample captured at the second outlet 16 by the flow cytometry.

The fluorescent micrograph in FIG. 5 illustrates the flow in the microfluid transfer channel 10. The non-Newtonian fluid prepared by dissolving λ-DNA in the Newtonian fluid contains green fluorescent particles having a size of 9.9 μm and red fluorescent particles having a size of 2.0 μm, and flows into one inlet. On the other hand, the Newtonian fluid (aqueous glycerin solution) flows into the other inlet. Herein, flow rates of the fluids are 40 μL/min and 80 μL/min, respectively.

According to the principle describe above, the green fluorescent material having a size of 9.9 μm may pass across the flow line at a considerably higher velocity than the red fluorescent particle having a size of 2.0 μm, thereby transferring toward a balance focusing point in Newtonian fluid flow.

The flow of two fluids out of the first outlet 15 and the second outlet 16 may be controlled so as to have a maximum efficiency by adjusting the flow rate ratio thereof through a clamp type valve for controlling an outlet pressure ratio.

As such, flow resistances at the first outlet and the second outlet may be adjusted by an alternation of design in a cross section of a flow path or utilizing a valve, so as to control a position of the flow line at which the non-Newtonian fluid and the Newtonian fluid are divided.

Herein, the green fluorescent particles were guided to flow out of the upper first outlet (Collection), while the red fluorescent particles were guided to flow out of the lower second outlet (Waste).

A ratio of relative numbers between the particles captured at the first and second outlets was determined by flow cytometry (FIGS. 6 and 7).

Herein, separation efficiencies of green fluorescent particles which are the target particles were determined as a recovery rate of 99.7% and a purity of 97.5%.

Further, according to Experimental Example 2 of the present invention, the experiment has proceeded with different densities of the target particles in the non-Newtonian fluid sample. The density of the target particles in the flow may be represented by a length fraction ($L_f$) as illustrated in Equation 6 below:

$$L_f = \frac{dAV_f}{V_{sp}} = \frac{6whV_f}{\pi d^2} \quad \text{[Equation 6]}$$

(wherein A is a cross-sectional area of the transfer channel, $V_f$ is a volume fraction of particles, $V_{sp}$ is an average volume of a single particle, and h is a height of the channel. The length fraction ($L_f$) is a terminology to efficiently describe that particles are densely focused into a single flow line. In this case, $L_f$ value may give intuitional understanding how long an average distance is present between the particles apart from each other in the transfer channel.)

Figure 8:
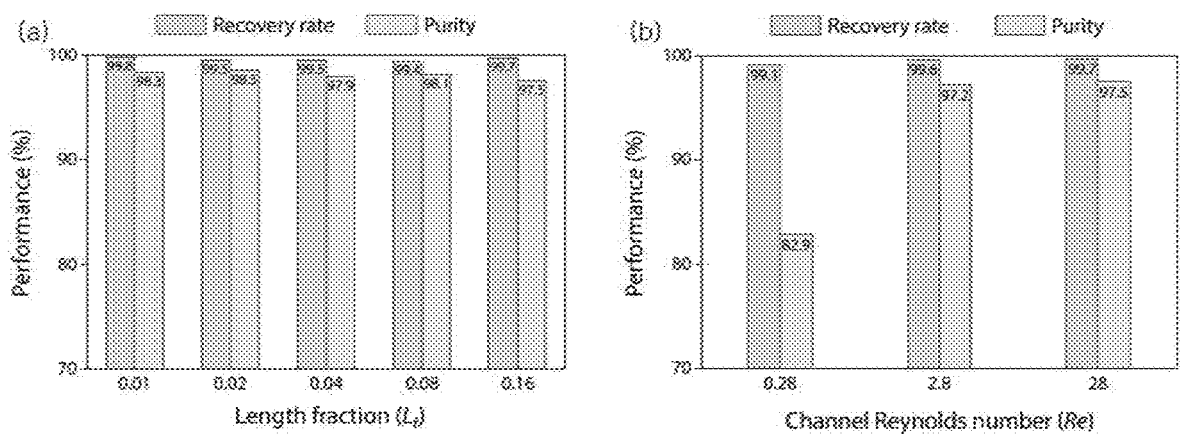
FIG. 8 are graphs illustrating measured results of particle separation efficiency depending upon changes in length fraction and a channel Reynolds number within the transfer channel.

FIG. 8 is graphs illustrating measured results of particle separation efficiency depending upon changes in the length fraction and the channel Reynolds number within the transfer channel.

Herein, FIG. 8(a) illustrates the recovery rate and purity when the length fraction varies from 0.01 to 0.16; and FIG. 8(b) illustrates the recovery and purity when the channel Reynolds number varies from 0.28 to 28.

Accordingly, the results of measuring particle separation efficiency with respect to various ranges of the length fraction ($L_f$) may be seen from the graph of FIG. 8(a).

Separation or transfer efficiencies of the target particles through the fluid chip having the transfer channel formed therein according to the present embodiment were not reduced even if the particle density is increased.

That is, when the density of target particles is the highest value ($L_f$=0.16), a treatment amount may be calculated at 6700 particles/sec. This value is substantially 16 times of a typical value in the conventional "Inertial Microfluidic Method" (reference 34) and, what is more, as high as 13000 times, compared to recently developed "Acoustophoretic Method" (reference 26).

In addition, as a result of investigating a change in the particle separation efficiency with respect to a change in the flow rate, it could be seen from the graph of FIG. 8(b) that particles may be separated with high efficiency not only in a high flow rate but also in an extremely low flow rate.

However, a condition of Re=0.28 is different from the mechanism for separating or transferring the target particles described hereinabove. This is because the inertial lift force ($F_L$) and the wall lift force ($F_W$) are very small, that is, substantially insignificant. Accordingly, it may be presumed from a success achieved under the condition of Re=0.28 that λ-DNA in the non-Newtonian fluid was deeply diffused into the Newtonian fluid to form a unique elastic lift force distribution, therefore, could push large particles more rapidly toward the wall on the Newtonian fluid side.

However, similar to a case of the high flow rate, effects of the inertial lift force to accelerate the separation and focusing of the target particles are insignificant, thus exhibiting low separation efficiency. According to this result, it could be seen that pumping a manual injector alone may enable high efficient separation, without continuously maintaining very strictly defined conditions for driving an apparatus having the transfer channel formed therein.

Therefore, according to the method for separating and washing microparticles via a stratified co-flow of non-Newtonian fluid and Newtonian fluid of the present invention, the microparticles may pass across the flow line and transfer from the non-Newtonian fluid to the Newtonian fluid by controlling the inertial lift forces and the elastic lift forces. As a result, native biofluids such as blood, serum, lymph could be received as those stand to directly separate particles such as cells. Consequently, any medium exchange or dilution process is not required.

Further, since a high particle density sample is treated under a high flow rate condition, an amount to be treated may be significantly increased. Referring to the number of particles to be treated per hour, the treated particles are as large as 16 times compared to the conventional "Inertial Microflidic method (reference 34)". Further, the number of treated particles is as large as 13000 times compared to the recently developed "Acoustophoretic Method (reference 26)." Nevertheless, the present invention may accomplish excellent separation or transfer efficiency with a recovery rate of 99% and a purity of 97%.

In addition, the present invention may efficiently come into action in a wide range of flow rate frequent to two orders of magnitude. For this reason, in a case of PBMC separation in which a centrifugal separation work should be continuously executed 4 times, leukocytes could be separated from the blood with a high efficiency even by simply pumping a manual injector at once without any centrifugal separation work, thereby accomplishing high efficient separation and washing processes by a simple hand work alone.

While the present invention has been described with reference to the preferred embodiments and modified examples, the present invention is not limited to the above-described specific embodiments and the modified examples, and it will be understood by those skilled in the related art that various modifications and variations may be made therein without departing from the scope of the present invention as defined by the appended claims, as well as these modifications and variations should not be understood separately from the technical spirit and prospect of the present invention.

DESCRIPTION OF REFERENCE NUMERALS

1: fluid chip,
10: transfer channel
11: first inlet,
12: second inlet
15: first outlet,
16: second outlet

REFERENCES

Eugene C. Butcher, I. L. W., Direct fluorescent labeling of cells with fluorescein or rhodamine isothiocyanate. I. Technical aspects. Journal of Immunological Methods, 1980. 37: p. 97-108.

Darzynkiewicz, Z., H. A. Crissman, and Z. Darynkiewicz, Flow Cytometry. Methods in Cell Biology. 1990: Elsevier Science & Technology.

De Clerck, L.S., et al., Use of fluorescent dyes in the determination of adherence of human leucocytes to endothelial cells and the effect of fluorochromes on cellular function. Journal of immunological methods, 1994. 172(1): p. 115-124.

Bossuyt, X., G. E. Marti, and T. A. Fleisher, Comparative analysis of whole blood lysis methods for flow cytometry. Cytometry, 1997. 30(3): p. 124-133.

Pugsley, W., et al., The impact of microemboli during cardiopulmonary bypass on neuropsychological functioning.

Reents, W., et al., Influence of different autotransfusion devices on the quality of salvaged blood. The Annals of thoracic surgery, 1999. 68(1): p. 58-62.

Petersson, F., et al., Carrier medium exchange through ultrasonic particle switching in microfluidic channels. Analytical chemistry, 2005. 77(5): p. 1216-1221.

Sista, R., et al., Development of a digital microfluidic platform for point of care testing. Lab Chip, 2008. 8(12): p. 2091-104.

Peterson, B. W., et al., Bacterial cell surface damage due to centrifugal compaction. Appl Environ Microbiol, 2012. 78(1): p. 120-5.

Sajeesh, P. and A. K. Sen, Particle separation and sorting in microfluidic devices: a review. Microfluidics and Nanofluidics, 2013. 17(1): p. 1-52.

Shields, C. W. t., C. D. Reyes, and G. P. Lopez, Microfluidic cell sorting: a review of the advances in the separation of cells from debulking to rare cell isolation. Lab Chip, 2015. 15(5): p. 1230-49.

Yamada, M., M. Nakashima, and M. Seki, Pinched flow fractionation: continuous size separation of particles utilizing a laminar flow profile in a pinched microchannel. Analytical chemistry, 2004. 76(18): p. 5465-5471.

Lu, X. and X. Xuan, Continuous Microfluidic Particle Separation via Elasto-Inertial Pinched Flow Fractionation. Anal Chem, 2015. 87(12): p. 6389-96.

Park, J.-S. and H.-I. Jung, Multiorifice flow fractionation: Continuous size-based separation of microspheres using a series of contraction/expansion microchannels. Analytical chemistry, 2009. 81(20): p. 8280-8288.

Kuntaegowdanahalli, S. S., et al., Inertial microfluidics for continuous particle separation in spiral microchannels. Lab Chip, 2009. 9(20): p. 2973-80.

Hur, S. C., et al., Deformability-based cell classification and enrichment using inertial microfluidics. Lab Chip, 2011. 11(5): p. 912-20.

Hsu, C. H., et al., Microvortex for focusing, guiding and sorting of particles. Lab Chip, 2008. 8(12): p. 2128-34.

Huang, L. R., et al., Continuous particle separation through deterministic lateral displacement. Science, 2004. 304(5673): p. 987-990.

Yang, S., A. Undar, and J. D. Zahn, A microfluidic device for continuous, real time blood plasma separation. Lab Chip, 2006. 6(7): p. 871-80.

Crowley, T. A. and V. Pizziconi, Isolation of plasma from whole blood using planar microfilters for lab-on-a-chip applications. Lab Chip, 2005. 5(9): p. 922-9.

Murthy, S. K., et al., Size-based microfluidic enrichment of neonatal rat cardiac cell populations. Biomed Microdevices, 2006. 8(3): p. 231-7.

Chen, X., et al., Microfluidic chip for blood cell separation and collection based on crossflow filtration. Sensors and Actuators B: Chemical, 2008. 130(1): p. 216-221.

Yamada, M. and M. Seki, Hydrodynamic filtration for on-chip particle concentration and classification utilizing microfluidics. Lab Chip, 2005. 5(11): p. 1233-9

Bhardwaj, P., P. Bagdi, and A. K. Sen, Microfluidic device based on a micro-hydrocyclone for particle-liquid separation. Lab Chip, 2011. 11(23): p. 4012-21

Lenshof, A., C. Magnusson, and T. Laurell, Acoustofluidics 8: applications of acoustophoresis in continuous flow microsystems. Lab Chip, 2012. 12(7): p. 1210-23.

Li, S., et al., Standing surface acoustic wave (SSAW)-based cell washing. Lab Chip, 2015. 15(1): p. 331-8.

Zborowski, M. and J. J. Chalmers, Rare cell separation and analysis by magnetic sorting. Anal Chem, 2011. 83(21): p. 8050-6.

Hoshino, K., et al., Microchip-based immunomagnetic detection of circulating tumor cells. Lab Chip, 2011. 11(20): p. 3449-57.

MacDonald, M., G. Spalding, and K. Dholakia, Microfluidic sorting in an optical lattice. Nature, 2003. 426(6965): p. 421-424.

Wang, X., et al., Enhanced cell sorting and manipulation with combined optical tweezer and microfluidic chip technologies. Lab Chip, 2011. 11(21): p. 3656-62.

Gascoyne, P. R. and J. Vykoukal, Particle separation by dielectrophoresis. Electrophoresis, 2002. 23(13): p. 1973.

Park, S., et al., Continuous dielectrophoretic bacterial separation and concentration from physiological media of high conductivity. Lab Chip, 2011. 11(17): p. 2893-900.

Hu, X., et al., Marker-specific sorting of rare cells using dielectrophoresis. Proc Natl AcadSci U S A, 2005. 102(44): p. 15757-61.

Gossett, D.R., et al., Inertial manipulation and transfer of microparticles across laminar fluid streams. Small, 2012. 8(17): p. 2757-64.

Yang, S., et al., Sheathlesselasto-inertial particle focusing and continuous separation in a straight rectangular microchannel. Lab Chip, 2011. 11(2): p. 266-73.

Bhagat, A. A. S., S. S. Kuntaegowdanahalli, and I. Papautsky, Enhanced particle filtration in straight microchannels using shear-modulated inertial migration. Physics of Fluids, 2008. 20(10): p. 101702.

What is claimed is:

1. A method for separating and washing microparticles via a stratified co-flow of non-Newtonian fluid and Newtonian fluid, comprising:
   flowing the non-Newtonian fluid and the Newtonian fluid in a stratified co-flow form within a transfer channel to induce a change in positions of particle focusing points at which forces acting on inside the transfer channel are balancing to each other; and
   separating or transferring target particles from microparticles included in the non-Newtonian fluid toward the Newtonian fluid,
   wherein the non-Newtonian fluid contains an artificial polymer, wherein the artificial polymer has sufficiently long relaxation time so as to have a larger elastic lift force with respect to the target particles than an inertial lift force, and
   the artificial polymer is contained in a concentration high enough to have a transfer velocity of the target particles sufficient to pass across a flow line,
   wherein the Newtonian fluid includes a fluid having a larger inertial lift force with respect to the target particles than an elastic lift force, and
   wherein the transfer channel has a height/width aspect ratio of greater than 1.

2. The method according to claim 1, wherein the artificial polymer is a water-soluble polymer having a relaxation time of 1 millisecond (ms) or more.

3. The method according to claim 2, wherein the artificial polymer includes at least one selected from λ-DNA, polyethylene oxide (PEO), and polyvinyl pyrrolidone (PVP).

4. The method according to claim 1, wherein the Newtonian fluid includes water, aqueous glycerin solution, or phosphate buffer saline (PBS).

5. The method according to claim 1, wherein an area ratio of cross-sectional areas occupied by the non-Newtonian fluid and the Newtonian fluid in the transfer channel is about 1:1.

* * * * *